US012211600B2

(12) United States Patent
Momoki (10) Patent No.: US 12,211,600 B2
(45) Date of Patent: Jan. 28, 2025

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Yohei Momoki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 344 days.

(21) Appl. No.: 17/898,408

(22) Filed: Aug. 29, 2022

(65) Prior Publication Data

US 2022/0415461 A1    Dec. 29, 2022

Related U.S. Application Data

(63) Continuation of application No. PCT/JP2021/008223, filed on Mar. 3, 2021.

(30) Foreign Application Priority Data

Mar. 3, 2020    (JP) .................................. 2020-036291

(51) Int. Cl.
  *G16H 15/00*    (2018.01)
  *G06T 7/00*    (2017.01)
  *G16H 30/40*    (2018.01)

(52) U.S. Cl.
  CPC .......... *G16H 15/00* (2018.01); *G06T 7/0012* (2013.01); *G16H 30/40* (2018.01); *G06T 2207/20092* (2013.01)

(58) Field of Classification Search
  CPC ...... G16H 15/00; G16H 30/40; G06T 7/0012; G06T 2207/20092

(Continued)

(56) References Cited

U.S. PATENT DOCUMENTS 7,187,790 B2 *   3/2007   Sabol ..................... G09B 23/28
                                                    382/128
11,257,584 B2 *   2/2022   Buckler ................ G06F 16/345
                  (Continued)

FOREIGN PATENT DOCUMENTS

JP     H11282936      10/1999
JP     2009082443      4/2009
       (Continued)

OTHER PUBLICATIONS

"International Search Report (Form PCT/ISA/210) of PCT/JP2021/008223," mailed on May 25, 2021, with English translation thereof, pp. 1-5.

(Continued)

*Primary Examiner* — Allen H Nguyen
(74) *Attorney, Agent, or Firm* — JCIPRNET (57) ABSTRACT

An information processing apparatus comprising at least one processor, wherein the at least one processor is configured to: derive, for each of predetermined property items, property information indicating a property of the property item from at least one image; receive, for each of the property items, a description regarding the property item to be selectable as to whether the description is necessary, unnecessary, or optional in a document; and generate a plurality of character string candidates including the description based on the property information regarding the property items that have been selected as the descriptions being necessary and optional by changing a combination of property items selected from among the property items that have been selected as the description being optional.

10 Claims, 4 Drawing Sheets

(58) Field of Classification Search
USPC .......................................................... 382/128
See application file for complete search history.

(56) References Cited

U.S. PATENT DOCUMENTS

| | | | | |
|---|---|---|---|---|
| 2006/0241353 | A1* | 10/2006 | Makino | G16H 15/00 |
| | | | | 600/300 |
| 2008/0052126 | A1* | 2/2008 | Sasai | G16H 30/20 |
| | | | | 707/E17.026 |
| 2010/0189366 | A1 | 7/2010 | Izuka et al. | |
| 2019/0279751 | A1 | 9/2019 | Nakamura et al. | |
| 2020/0302117 | A1* | 9/2020 | Hu | G16H 30/40 |
| 2020/0342967 | A1* | 10/2020 | Bronkalla | G16H 15/00 |

FOREIGN PATENT DOCUMENTS

| | | |
|---|---|---|
| JP | 2016021216 | 2/2016 |
| JP | 2019153250 | 9/2019 |

OTHER PUBLICATIONS

"Written Opinion of the International Searching Authority (Form PCT/ISA/237)" of PCT/JP2021/008223, mailed on May 25, 2021, with English translation thereof, pp. 1-6.

* cited by examiner

INFORMATION PROCESSING APPARATUS, INFORMATION PROCESSING METHOD, AND INFORMATION PROCESSING PROGRAM

CROSS REFERENCE TO RELATED APPLICATIONS

The present application is a Continuation of PCT International Application No. PCT/JP2021/008223, filed on Mar. 3, 2021, which claims priority to Japanese Patent Application No. 2020-036291, filed on Mar. 3, 2020. Each application above is hereby expressly incorporated by reference, in its entirety, into the present application.

BACKGROUND

Technical Field

The present disclosure relates to an information processing apparatus, an information processing method, and an information processing program for supporting the creation of documents such as interpretation reports.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, image diagnosis is made by analyzing a medical image via computer-aided diagnosis (CAD) using a discriminator in which learning is performed by deep learning or the like, and discriminating properties such as the shape, density, position, and size of a structure of interest such as a lesion included in the medical image. The analysis result obtained in this way is saved in a database in association with examination information, such as a patient name, gender, age, and an imaging apparatus which has acquired a medical image. The medical image and the analysis result are transmitted to a terminal of a radiologist who interprets the medical images. The radiologist interprets the medical image by referring to the distributed medical image and analysis result and creates an interpretation report, in his or her own interpretation terminal.

Meanwhile, with the improvement of the performance of the CT apparatus and the MRI apparatus described above, the number of medical images to be interpreted is increasing. Therefore, in order to reduce the burden of the interpretation work of a radiologist, various methods have been proposed to support the creation of medical documents such as interpretation reports. For example, a method for generating a sentence to be included in an interpretation report based on keywords input by a radiologist and on information indicating a property of a structure of interest such as a lesion (hereinafter referred to as property information) included in an analysis result of a medical image is disclosed (see JP2019-153250A). In the technique described in JP2019-153250A, a sentence to be included in the interpretation report is created by using a learning model in which machine learning is performed, such as a recurrent neural network trained to generate a sentence from characters representing the input property information.

However, the sentence generated by the learning model described in JP2019-153250A is not always the sentence desired by the radiologist. For example, some radiologists prefer a concise interpretation report in which only important findings are described, while others prefer a complete interpretation report in which all positive findings are described.

SUMMARY

The present disclosure provides an information processing apparatus, an information processing method, and an information processing program capable of supporting creation of documents such as interpretation reports.

According to a first aspect of the present disclosure, there is provided an information processing apparatus comprising at least one processor, in which the processor is configured to derive, for each of predetermined property items, property information indicating a property of the property item from at least one image, receive, for each of the property items, a description regarding the property item to be selectable as to whether the description is necessary, unnecessary, or optional in a document, and generate a plurality of character string candidates including the description based on the property information regarding the property items that have been selected as the descriptions being necessary and optional by changing a combination of property items selected from among the property items that have been selected as the description being optional.

According to a second aspect of the present disclosure, in the above aspect, the processor may be configured to construct the combination such that a character string satisfying a predetermined rule is included as one of the character string candidates.

According to a third aspect of the present disclosure, in the above second aspect, the rule may be a rule regarding the number of the property items included in the character string candidates.

According to a fourth aspect of the present disclosure, in the above second and third aspects, the rule may be a rule regarding a priority set for each property item.

According to a fifth aspect of the present disclosure, in the above second to fourth aspects, the processor may be configured to derive a property score indicating a prominence of the property of the property item, and the rule may be a rule regarding the property score.

According to a sixth aspect of the present disclosure, in the above second to fifth aspects, the rule may be a rule regarding a relationship between the property items.

According to a seventh aspect of the present disclosure, in the above aspects, the processor may be configured to perform control such that the character string candidates are displayed on a display.

According to an eighth aspect of the present disclosure, the above second to sixth aspects, the processor may be configured to perform control such that the character string candidates are displayed on a display by arranging the character string candidates in an order of a compliance rate of the rule.

According to a ninth aspect of the present disclosure, there is provided an information processing method, comprising: deriving, for each of predetermined property items, property information indicating a property of the property item from at least one image; receiving, for each of the property items, a description regarding the property item to be selectable as to whether the description is necessary, unnecessary, or optional in a document; and generating a plurality of character string candidates including the description based on the property information regarding the property items that have been selected as the descriptions being necessary and optional by changing a combination of property items selected from among the property items that have been selected as the description being optional.

According to a tenth aspect of the present disclosure, there is provided an information processing program for causing a computer to execute a process comprising: deriving, for each of predetermined property items, property information indicating a property of the property item from at least one image; receiving, for each of the property items, a description regarding the property item to be selectable as to whether the description is necessary, unnecessary, or optional in a document; and generating a plurality of character string candidates including the description based on the property information regarding the property items that have been selected as the descriptions being necessary and optional by changing a combination of property items selected from among the property items that have been selected as the description being optional.

According to the above aspects, the information processing apparatus, information processing method, and information processing program of the present disclosure can support the creation of documents such as interpretation reports.

DETAILED DESCRIPTION

Hereinafter, each exemplary embodiment of the present disclosure will be described with reference to the drawings.

First, a configuration of a medical information system 1 to which an information processing apparatus of the present disclosure is applied will be described.

Figure 1:
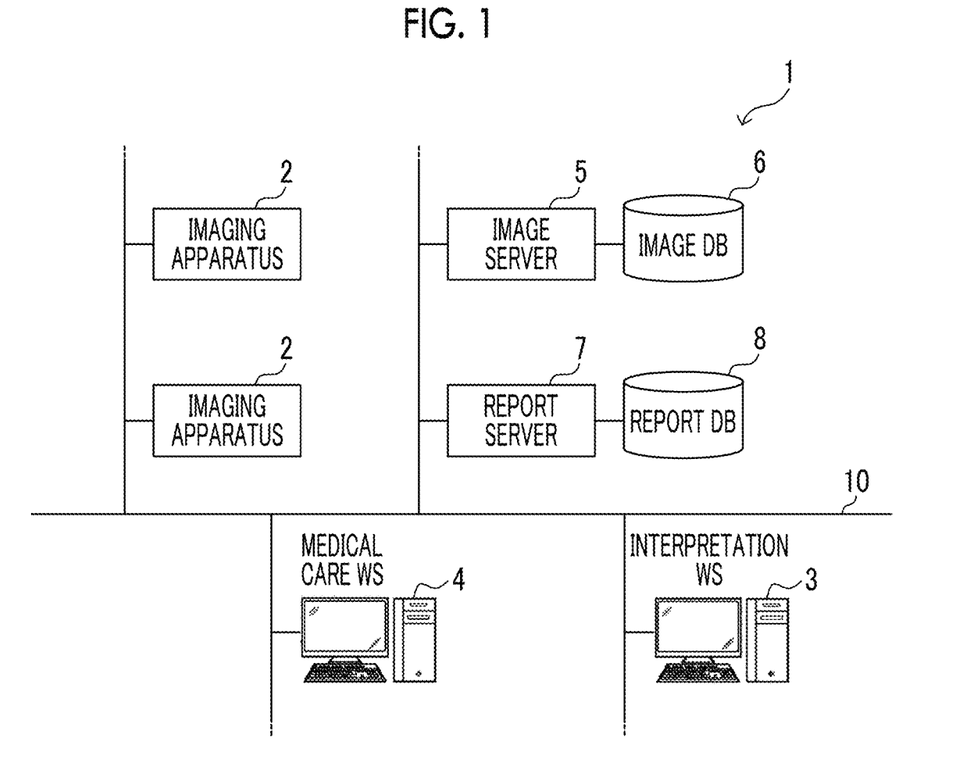
FIG. 1 is a diagram showing an example of a schematic configuration of a medical information system according to an exemplary embodiment.

FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, the medical information system 1 is configured to include a plurality of imaging apparatuses 2, a plurality of interpretation work stations (WS) 3 that are interpretation terminals, a medical care WS 4, an image server 5, an image database (DB) 6, a report server 7, and a report DB 8, which are connected via a wired or wireless network 10 so as to be able to communicate with each other.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded and installed on the computer in response to a request.

The imaging apparatus 2 is an apparatus (modality) that generates a medical image showing a diagnosis target part of the subject by imaging the diagnosis target part. Specifically, examples of the imaging apparatus include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of the radiology department to interpret a medical image and to create an interpretation report, and encompasses an information processing apparatus 20 (which will be described in detail later) according to the present exemplary embodiment. In the interpretation WS 3, a viewing request for a medical image to the image server 5, various image processing for the medical image received from the image server 5, display of the medical image, and input reception of comments on findings regarding the medical image are performed. In the interpretation WS 3, an analysis process for medical images, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by, for example, a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, and property information (which will be described in detail later).

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Next, the information processing apparatus 20 according to the present exemplary embodiment will be described.

Figure 2:
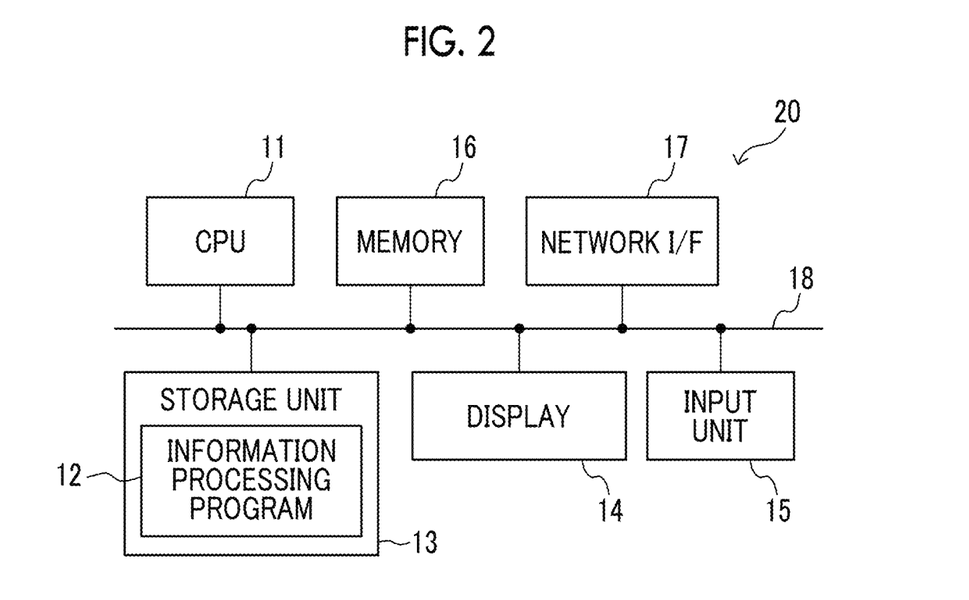
FIG. 2 is a block diagram showing an example of a hardware configuration of an information processing apparatus according to an exemplary embodiment.

First, with reference to FIG. 2, a hardware configuration of the information processing apparatus 20 according to the present exemplary embodiment will be described. As shown in FIG. 2, the information processing apparatus 20 includes a central processing unit (CPU) 11, a non-volatile storage unit 13, and a memory 16 as a temporary storage area. Further, the information processing apparatus 20 includes a display 14 such as a liquid crystal display and an organic electro luminescence (EL) display, an input unit 15 such as a keyboard and a mouse, and a network interface (I/F) 17 connected to the network 10. The CPU 11, the storage unit 13, the display 14, the input unit 15, the memory 16, and the network I/F 17 are connected to a bus 18. The CPU 11 is an example of a processor in the present disclosure.

The storage unit 13 is realized by a storage apparatus such as a hard disk drive (HDD), a solid state drive (SSD), and a flash memory. An information processing program 12 is stored in the storage unit 13 as the storage medium. The CPU 11 reads out the information processing program 12 from the storage unit 13, loads the read-out program into the memory 16, and executes the loaded information processing program 12.

Figure 3:
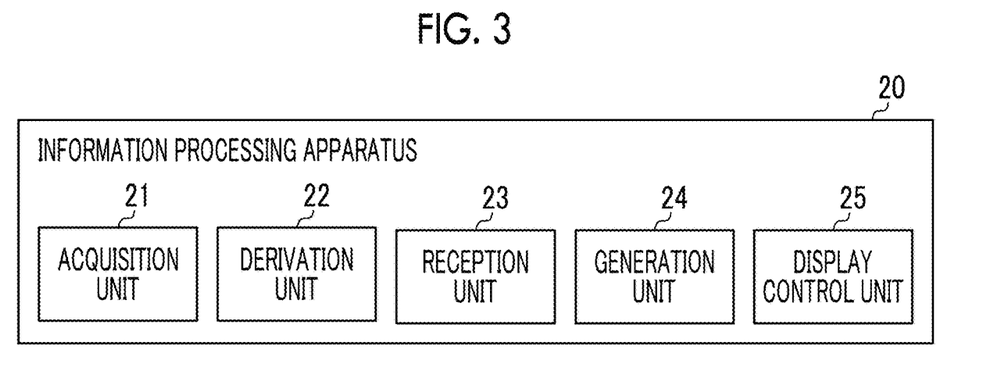
FIG. 3 is a block diagram showing an example of a functional configuration of the information processing apparatus according to an exemplary embodiment.
Figure 4:
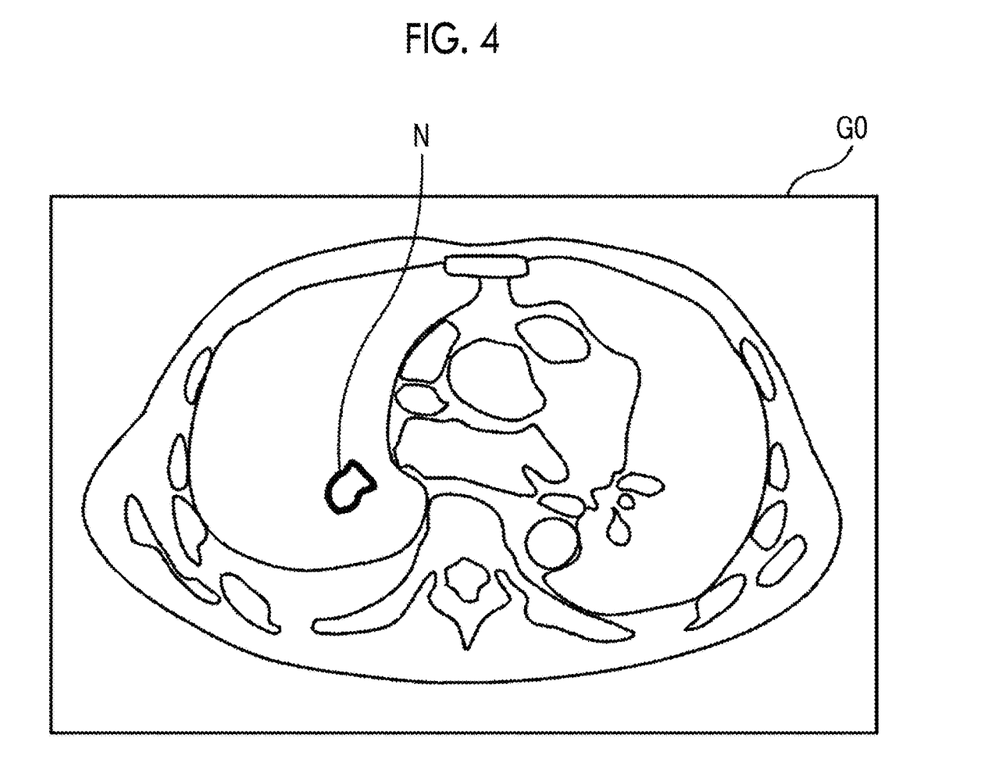
FIG. 4 is a diagram schematically showing a medical image.

Next, with reference to FIGS. 3 to 5, a functional configuration of the information processing apparatus 20 according to the present exemplary embodiment will be described. As shown in FIG. 3, the information processing apparatus 20 includes an acquisition unit 21, a derivation unit 22, a reception unit 23, a generation unit 24, and a display control unit 25. The CPU 11 executing the information processing program 12 functions as the acquisition unit 21, the derivation unit 22, the reception unit 23, the generation unit 24, and the display control unit 25.

Figure 5:
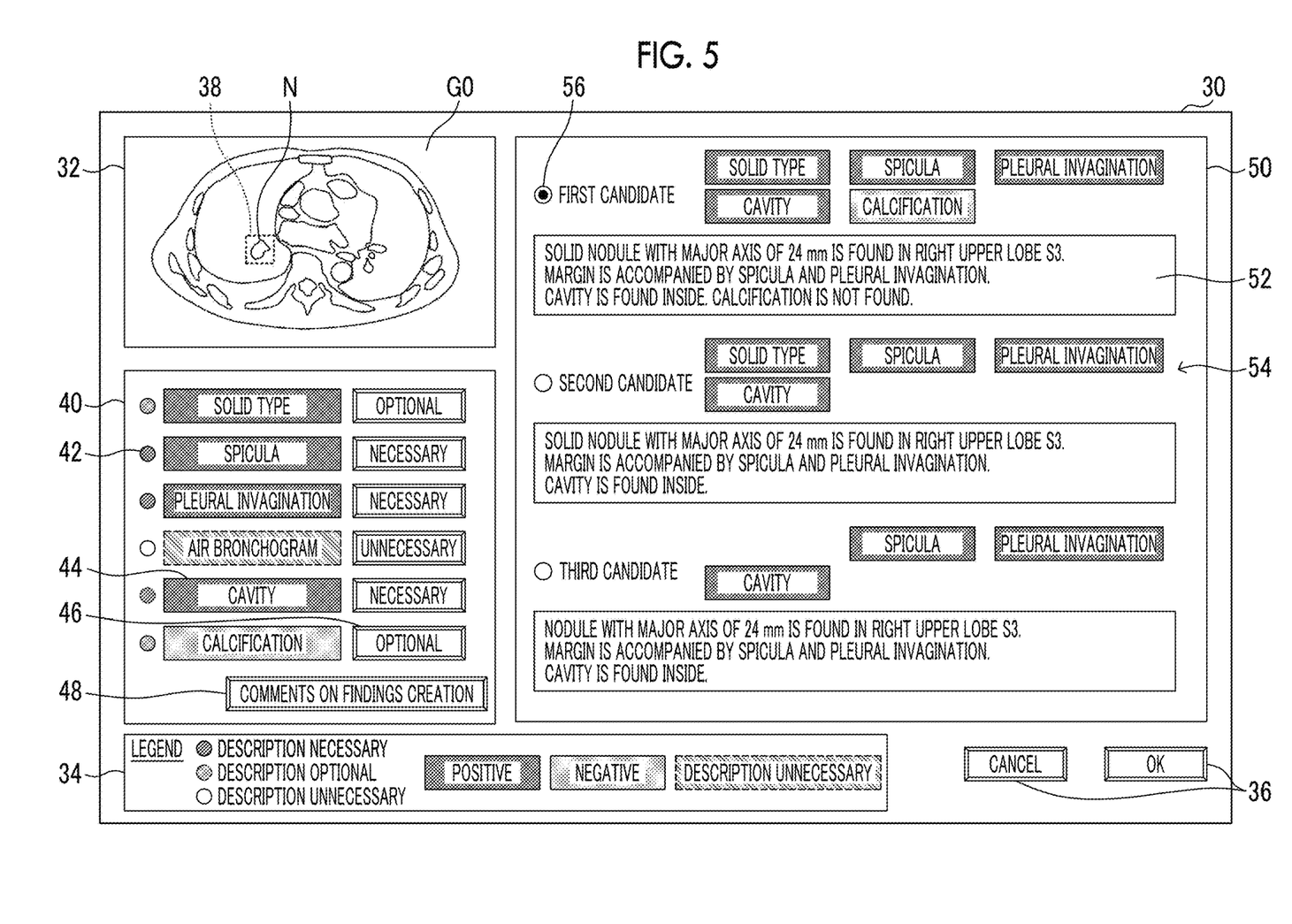
FIG. 5 is a diagram showing an example of a screen for creating an interpretation report according to an exemplary embodiment.

FIG. 5 is a diagram showing an example of the interpretation report creation screen 30 displayed on the display 14. The creation screen 30 includes an image area 32 on which a medical image is displayed, a reception area 40 on which a property item 44 and a reception means 46 (details will be described later) are displayed, a comment-on-findings area 50 in which candidates of comments on findings are displayed, and a cancel and OK button 36. Hereinafter, the functions of the acquisition unit 21, the derivation unit 22, the reception unit 23, the generation unit 24, and the display control unit 25 will be described with reference to FIG. 5.

The acquisition unit 21 acquires a medical image G0 as an example of the image from the image server 5 via the network I/F 17. FIG. 4 is a diagram schematically showing the medical image G0. In the present exemplary embodiment, as an example, a CT image of a lung is used as the medical image G0. The medical image G0 includes a nodular shadow N as an example of a structure of interest such as a lesion.

The derivation unit 22 derives property information indicating a property of the property item 44 for each predetermined property item 44 from at least one medical image G0. Specifically, the derivation unit 22 analyzes the medical image G0 via CAD or the like, and specifies the position, type, and size of the lesion included in the medical image G0. Then, a property score indicating the prominence of a property of a predetermined property item 44 regarding a specified lesion is derived, and the property information indicating the property of the property item 44 is derived based on the property score. The property information is information showing the result of determining whether the property is positive or negative, for example, depending on whether the property score is equal to or higher than a predetermined threshold value. The property item 44 is an item that is predetermined and stored in the storage unit 13 according to at least one of the position, type, or size of the lesion.

As shown in FIG. 5, the display control unit 25 performs control such that the medical image G0 acquired by the acquisition unit 21 is displayed in the image area 32. Further, the display control unit 25 controls the display in the reception area 40 such that the user can check the property information for each property item 44 based on the property information derived by the derivation unit 22.

FIG. 5 shows, as an example of the property item 44 related to the nodular shadow N, the presence or absence of solid type, spicula, pleural invagination, air bronchogram, cavity, and calcification. An example is shown in which these property items 44 are color-coded (see Legend 34) and displayed as positive or negative based on the property information. The method of displaying the property information by the display control unit 25 is not limited thereto, and for example, characters and marks indicating positive or positive may be displayed for each property item. In addition, for example, a property score may be used as the property information and displayed in a gradation in which the color becomes darker as the property becomes more prominent.

Incidentally, in the case of supporting the creation of an interpretation report, it is desirable to generate a plurality of comment-on-findings candidates whose description contents are changed according to the intention and preference of the radiologist who creates the interpretation report. For example, some radiologists prefer a concise interpretation report in which only important findings are described, while others prefer a complete interpretation report in which all positive findings are described.

Therefore, the reception unit 23 receives, for each property item 44, a description regarding the property item 44 to be selectable as to whether the description is necessary, unnecessary, or optional in a document. As shown in FIG. 5, the display control unit 25 controls the reception unit 23 such that the reception means 46 for receiving the selection of the description being necessary, unnecessary, or optional for each property item 44 is displayed in the reception area 40. For example, the reception means 46 may be a button that transitions from the initial value "optional" to "necessary", "unnecessary, "optional", . . . by left-clicking the mouse as an example of the input unit 15, and transitions in the reverse order by right-clicking. Further, for example, the reception means 46 may be a pull-down list for selecting any one of "necessary", "unnecessary", and "optional", a radio button, and the like.

The initial value of the reception means 46 is not limited to "optional", and for example, a property item that requires description and a property item having a high priority of description may be set in advance for each property item 44, such as "necessary". Further, by learning the setting history of the reception means 46 by the user, a value with a high frequency of setting may be set as an initial value.

Further, as shown in FIG. 5, the display control unit 25 may display, for each property item 44, an icon 42 (see Legend 34) indicating the description being necessary, unnecessary, or optional that has been currently selected so that the user can easily identify it. Further, as shown in FIG. 5, the display control unit 25 may change the color and frame of the property item 44 selected as the description being unnecessary by the user so that the user can easily identify it.

The user selects "necessary", "unnecessary", or "optional" for each property item 44 by operating the reception means 46 via the input unit 15 while checking the property information displayed in the reception area 40 (the color of the property item 44 in the example of FIG. 5). That is, in addition to selecting a property item that requires description and a property item that omits description, the user can make a selection that entrusts the information processing apparatus 20 to determine whether or not the description is necessary. Then, in a case where the user finishes the operation of the reception means 46, the user presses a comment-on-findings creation button 48.

In a case where the comment-on-findings creation button 48 is pressed, the generation unit 24 generates a plurality of comment-on-findings candidates 52 as an example of character strings including the description based on the property information regarding the property items 44 that have been selected as the descriptions being necessary and optional by changing a combination of the property items 44 selected from among the property items 44 that have been selected as the description being optional. As a method of generating the comment-on-findings candidate 52 by using the generation unit 24, for example, a learning model in which machine learning is performed, such as the recurrent neural network described in JP2019-153250A can be applied. In the case of applying such a learning model, the comment-on-findings candidate 52 may be generated by the generation unit 24 analyzing the medical image G0 via CAD or the like separately from the analysis performed by the derivation unit 22, and inputting the result of the analysis performed by the generation unit 24 into the learning model. Further, the comment-on-findings candidate 52 may be generated by inputting the result of the analysis performed by the derivation unit 22 into the learning model.

The display control unit 25 performs control such that the plurality of comment-on-findings candidates 52 generated by the generation unit 24 are displayed in the comment-on-findings area 50. In FIG. 5, an example is shown in which three comment-on-findings candidates 52 generated by changing the combination of whether or not to describe "solid type" and "calcification", which are the property items 44 that have been selected as the description being optional, are displayed. The comments on findings of the first candidate include descriptions regarding "solid type" and "calcification". The comments on findings of the second candidate include a description regarding "solid type" but not a description regarding "calcification". The comments on findings of the third candidate do not include descriptions regarding "solid type" and "calcification".

In addition, it is preferable that the generation unit 24 constructs a combination of the property items 44 selected from among the property items 44 that have been selected as the description being optional such that the comments on findings satisfying a predetermined rule are included as any of the comment-on-findings candidates 52. That is, the rule defines a criterion for determining which property item 44 is included in the comment-on-findings candidates 52 among the property items 44 that have been selected as the description being optional. It is sufficient that any one of the comment-on-findings candidates 52 generated by the generation unit 24 is generated so as to satisfy the rule, and all the comment-on-findings candidates 52 do not necessarily satisfy the rule.

As an example of the rule, there is a rule regarding the number of the property items 44 included in the comment-on-findings candidate 52. In this case, the generation unit 24 selects the property item to be included in the comment-on-findings candidate 52 from among the property items 44 that have been selected as the description being optional such that the number of the property items 44 included in the comment-on-findings candidate 52 satisfies the rule. By providing a rule regarding the number of the property items 44, for example, the comment-on-findings candidate 52 can be generated so as not to be too long and not too short.

Further, as an example of the rule, there is a rule regarding the priority set for each property item 44. For example, rules may be set such as lowering the priority of the description because whether or not it is "solid type" can be determined by looking at the medical image G0, and increasing the priority of the description because malignancy is suspected in the case where "spicula" is found. In this case, the generation unit 24 may select the property item 44 having a relatively high priority from among the property items 44 that have been selected as the description being optional as the property item to be included in the comment-on-findings candidate 52. Thereby, the comment-on-findings candidate 52 including the description regarding the property item 44 having a high priority can be generated.

Further, as an example of the rule, there is a rule regarding the property score. As described above, the property score is a score indicating the prominence of the property of the property item 44. For example, a rule may be defined in which the description regarding the property item 44 whose property score is equal to or higher than the threshold value is preferentially included in the comment-on-findings candidate 52. In this case, the generation unit 24 may select the property item 44 whose property score is equal to or higher than the threshold value from among the property items 44 that have been selected as the description being optional as the property item to be included in the comment-on-findings candidate 52. Thereby, the comment-on-findings candidate 52 with high reliability of the content can be generated.

In addition, as an example of the rule, there is a rule regarding the relationship between the property items 44. For example, in a case where the nodular shadow N is a frosted glass-like nodule, calcification is usually not found. Therefore, for example, in a case where it is determined from the property information that the nodular shadow N is likely to be frosted glass-like, a rule may be set so as not to make description regarding calcification. In this case, in the case where it is determined that the nodular shadow N is likely to be frosted glass-like, the generation unit 24 may exclude "calcification" that has been selected as the description being optional from the property items to be included in the comment-on-findings candidate 52. Thereby, the comment-on-findings candidate 52 in which the description regarding calcification is omitted can be generated.

Note that each of the above-mentioned rules is an example and is not limited to these, and these may be selectively used in combination. In addition, the rule may be a predetermined rule or may be a predetermined rule selected by the user. For example, prior to the generation of the comment-on-findings candidate 52 performed by the generation unit 24, a screen provided with a check box for selecting any rule from a plurality of predetermined rules may be displayed on the display 14 and the selection by the user may be received.

Further, desirably, the display control unit 25 performs control such that the comment-on-findings candidates 52 are displayed in the comment-on-findings area 50 by arranging them in the order of the rule compliance rate. Further, the display control unit 25 may perform control such that the comment-on-findings candidate 52 having the highest rule compliance rate among the plurality of comment-on-findings candidates 52 is emphasized and displayed on the display. Further, as shown in FIG. 5, the display control unit 25 may display a list 54 of the property items 44 including the description in each comment-on-findings candidate 52 in the comment-on-findings area 50.

The user selects a desired comment-on-findings candidate 52 with a radio button 56 while referring to the comment-on-findings candidate 52 and the list 54, and presses the OK button 36. Thereby, an interpretation report including the medical image G0 and the comment-on-findings candidate 52 selected by the user is created.

Figure 6:
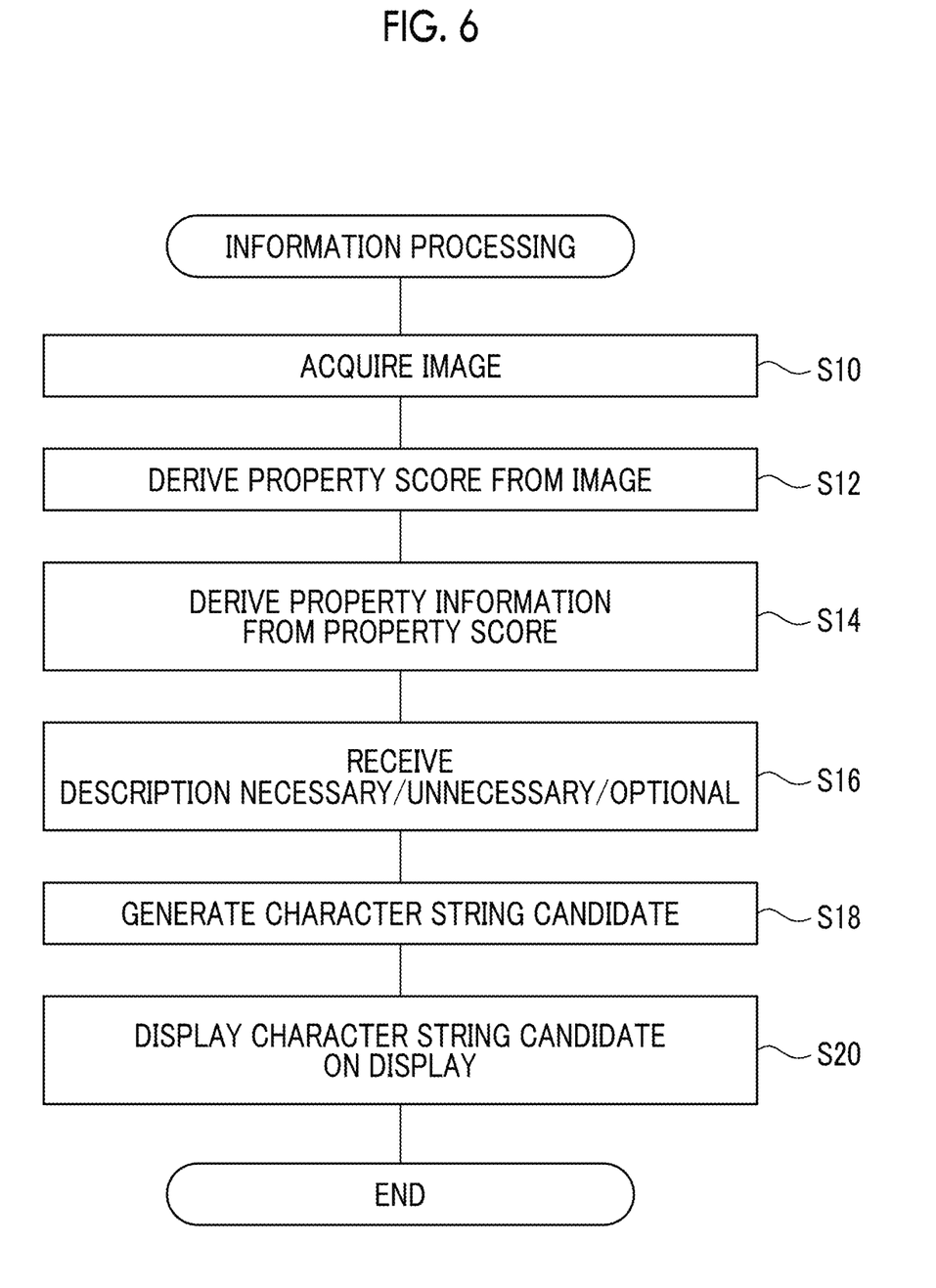
FIG. 6 is a flowchart showing an example of information processing according to an exemplary embodiment.

Next, with reference to FIG. 6, operations of the information processing apparatus 20 according to the present exemplary embodiment will be described. The CPU 11 executes the information processing program 12, and thus, the information processing shown in FIG. 6 is executed. The information processing shown in FIG. 6 is executed, for example, in a case where an instruction to start creating an interpretation report for the medical image G0 is input via the input unit 15.

In Step S10 of FIG. 6, the acquisition unit 21 acquires the medical image G0 from the image server 5. In Step S12, the derivation unit 22 specifies the position, type, and size of the lesion included in the medical image G0 acquired in Step S10, and derives a property score indicating the prominence of the properties of predetermined property items related to the specified lesion. In Step S14, the derivation unit 22 derives the property information indicating the property of the property item from the property score derived in Step S12.

In Step S16, the reception unit 23 receives, for each property item, selection of a description regarding the property item as to whether the description is necessary, unnecessary, or optional in the document. In Step S18, the generation unit 24 generates a plurality of comment-on-findings candidates 52 including the description based on the property information derived in Step S14 regarding the property items that have been selected as the descriptions being necessary and optional in Step S16 by changing a combination of the property items selected from among the property items that have been selected as the description being optional. In Step S20, the display control unit 25 performs control such that the comment-on-findings candidate 52 generated in Step S18 is displayed on the display 14, and ends the process.

As described above, the information processing apparatus 20 according to the exemplary embodiment of the present disclosure derives property information indicating the property of the property item for each predetermined property item from at least one medical image G0. In addition, for each of the property items, a description regarding the property item is received to be selectable as to whether the description is necessary, unnecessary, or optional in a document. In addition, a plurality of character string candidates including the description based on the property information regarding the property items that have been selected as the descriptions being necessary and optional are generated by changing a combination of the property items selected from among the property items that have been selected as the description being optional. According to such a form, since a plurality of comment-on-findings candidates having contents desired by the radiologist can be presented, it is possible to support the creation of a document such as an interpretation report.

In the above exemplary embodiment, in the case where the user finishes the operation of the reception means 46 and presses the comment-on-findings creation button 48, the generation unit 24 starts generation of the comment-on-findings candidate 52, but the present disclosure is not limited thereto. For example, the comment-on-findings candidate 52 may be generated in real time each time the user operates the reception means 46.

Further, although the derivation unit 22 specifies the position of the lesion included in the medical image G0 in the above exemplary embodiments, the present disclosure is not limited thereto. For example, the user may select a region of interest in the medical image G0 via the input unit 15, and the derivation unit 22 may determine the properties of the property items of the lesion included in the selected region. According to such a form, for example, even in a case where one medical image G0 includes a plurality of lesions, it is possible to create comment-on-findings candidates for the lesion desired by the user.

Further, in each of the above exemplary embodiments, the display control unit 25 may generate an image in which a mark indicating the position of the lesion specified by the derivation unit 22 is added to the medical image G0. In the example of FIG. 5, the nodular shadow N included in the medical image G0 is surrounded by a broken-line rectangle mark 38. This makes it easier, for example, for a reader of the interpretation report to see the region in the image that is the basis of the lesion, without the need for the radiologist to provide comments on findings related to the position of the lesion. Therefore, it is possible to support the creation of a document such as an interpretation report. The mark 38 indicating the positions of the lesion is not limited to the broken-line rectangle, but may be various marks such as, for example, a polygon, a circle, an arrow, or the like, and the line type of the mark (a solid line, a broken line, and a dotted line), line color, line thickness, or the like may be changed as appropriate.

Further, in the above exemplary embodiment, the present disclosure is applied in the case where the interpretation report is created as a document and the comments on findings are generated as a character string, but the present disclosure is not limited thereto. For example, the present disclosure may be applied in the case of creating a medical document other than an interpretation report, such as an electronic medical record and a diagnosis report, and other documents including a character string related to an image. Further, for example, instead of the comment on findings, a keyword as shown in the list 54 of the property item 44 in FIG. 5 may be generated.

Further, although the various processes are performed using the medical image G0 with a lung as the diagnosis target in the above exemplary embodiments, the diagnosis target is not limited to the lung. In addition to the lung, any part of a human body such as a heart, liver, brain, and limbs can be diagnosed. Further, although various processes are performed using one medical image G0 in the above exemplary embodiments, various processes may be performed using a plurality of images such as a plurality of tomographic images relating to the same diagnosis target.

Further, in each of the above exemplary embodiments, each process of the derivation unit 22 and the generation unit 24 in the information processing apparatus 20 encompassed in the interpretation WS 3 may be performed by an external device, for example, another analysis server connected to the network 10. In this case, the external device acquires the medical image G0 from the image server 5, and derives the property information indicating the property of the property item for each predetermined property item from the medical image G0. Further, the comment-on-findings candidate 52 is generated based on the information that has been selected as the description regarding the property item being necessary, unnecessary, or optional in the document, for each property item received by the information processing apparatus 20. In the information processing apparatus 20, the display control unit 25 controls the display content to be displayed on the display 14 based on the property information derived by the external device and the comment-on-findings candidate 52 generated by the external device.

In the above exemplary embodiments, for example, as hardware structures of processing units that execute various kinds of processing, such as the acquisition unit 21, the derivation unit 22, the reception unit 23, the generation unit 24, and the display control unit 25, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor. As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

The disclosure of JP2020-036291 filed on Mar. 3, 2020 is incorporated herein by reference in its entirety. All literatures, patent applications, and technical standards described herein are incorporated by reference to the same extent as if the individual literature, patent applications, and technical standards were specifically and individually stated to be incorporated by reference.

What is claimed is:

1. An information processing apparatus comprising at least one processor, wherein the at least one processor is configured to:
   derive, for each of predetermined property items, property information indicating a property of the property item from at least one image;
   receive, for each of the property items, a description regarding the property item to be selectable as to whether the description is necessary, unnecessary, or optional in a document; and
   generate a plurality of character string candidates including the description based on the property information regarding the property items that have been selected as the descriptions being necessary and optional by changing a combination of property items selected from among the property items that have been selected as the description being optional.

2. The information processing apparatus according to claim 1, wherein the at least one processor is configured to construct the combination such that a character string satisfying a predetermined rule is included as one of the character string candidates.

3. The information processing apparatus according to claim 2, wherein the rule is a rule regarding the number of the property items included in the character string candidates.

4. The information processing apparatus according to claim 2, wherein the rule is a rule regarding a priority set for each property item.

5. The information processing apparatus according to claim 2, wherein:
the at least one processor is configured to derive a property score indicating a prominence of the property of the property item, and
the rule is a rule regarding the property score.

6. The information processing apparatus according to claim 2, wherein the rule is a rule regarding a relationship between the property items.

7. The information processing apparatus according to claim 1, wherein the at least one processor is configured to perform control such that the character string candidates are displayed on a display.

8. The information processing apparatus according to claim 2, wherein the at least one processor is configured to perform control such that the character string candidates are displayed on a display by arranging the character string candidates in an order of a compliance rate of the rule.

9. An information processing method comprising:
deriving, for each of predetermined property items, property information indicating a property of the property item from at least one image;
receiving, for each of the property items, a description regarding the property item to be selectable as to whether the description is necessary, unnecessary, or optional in a document; and
generating a plurality of character string candidates including the description based on the property information regarding the property items that have been selected as the descriptions being necessary and optional by changing a combination of property items selected from among the property items that have been selected as the description being optional.

10. A non-transitory computer-readable storage medium storing an information processing program for causing a computer to execute a process comprising:
deriving, for each of predetermined property items, property information indicating a property of the property item from at least one image;
receiving, for each of the property items, a description regarding the property item to be selectable as to whether the description is necessary, unnecessary, or optional in a document; and
generating a plurality of character string candidates including the description based on the property information regarding the property items that have been selected as the descriptions being necessary and optional by changing a combination of property items selected from among the property items that have been selected as the description being optional.

* * * * *